US00PP29075P3

(12) United States Plant Patent
Hofmann

(10) Patent No.: US PP29,075 P3
(45) Date of Patent: Mar. 6, 2018

(54) ***CALIBRACHOA* PLANT NAMED 'INCALIMRED'**

(50) Latin Name: ***Calibrachoa* sp.**
Varietal Denomination: INCALIMRED

(71) Applicant: Birgit Hofmann, Rudesheim am Rhein (DE)

(72) Inventor: Birgit Hofmann, Rudesheim am Rhein (DE)

(73) Assignee: Innovaplant Zierpflanxen GmbH & Co. KG, Gensingen (DE)

( * ) Notice: Subject to any disclaimer, the term of this patent is extended or adjusted under 35 U.S.C. 154(b) by 47 days.

(21) Appl. No.: 14/999,772

(22) Filed: Jun. 24, 2016

(65) Prior Publication Data

US 2017/0374784 P1 Dec. 28, 2017

(51) Int. Cl.
*A01H 5/02* (2006.01)

(52) U.S. Cl.
USPC ..... Plt./413
CPC ..... *A01H 5/02* (2013.01)

(58) Field of Classification Search
USPC ..... Plt./413
See application file for complete search history.

*Primary Examiner* — Keith O Robinson
(74) *Attorney, Agent, or Firm* — C. A. Whealy

(57) ABSTRACT

A new and distinct *Calibrachoa* plant named 'INCALIMRED', characterized by its upright to outwardly spreading and low mounding to eventually trailing plant habit; vigorous growth habit; freely branching habit; dense and bushy appearance; early and freely flowering habit; large dark red-colored petals with a dark burgundy-colored central band and yellow-colored centers; and good garden performance.

1 Drawing Sheet

Botanical designation: *Calibrachoa* sp.
Cultivar denomination: 'INCALIMRED'.

BACKGROUND OF THE INVENTION

The present invention relates to a new and distinct cultivar of *Calibrachoa* plant, botanically known as *Calibrachoa* sp. and hereinafter referred to by the name 'INCALIMRED'.

The new *Calibrachoa* plant is a product of a planned breeding program conducted by the Inventor in Heidesheim, Germany. The objective of the breeding program is to create new uniform, vigorous, freely-branching and early-flowering *Calibrachoa* plants with large attractive flowers and good garden performance.

The new *Calibrachoa* plant originated from a cross-pollination conducted by the Inventor in Heidesheim, Germany in December, 2013 of *Calibrachoa* sp. 'Duealcher', disclosed in U.S. Plant Pat. No. 25,522, as the female, or seed, parent with a proprietary selection of *Calibrachoa* sp. identified as code number Ca12-3023-4, not patented, as the male, or pollen, parent. The new *Calibrachoa* plant was discovered and first selected by the Inventor as a single flowering plant within the progeny of the stated cross-pollination in a controlled greenhouse environment in Heidesheim, Germany in June, 2014.

Asexual reproduction of the new *Calibrachoa* plant by vegetative terminal cuttings in a controlled greenhouse environment in Gensingen, Germany since June, 2014 has shown that the unique features of this new *Calibrachoa* plant are stable and reproduced true to type in successive generations.

SUMMARY OF THE INVENTION

Plants of the new *Calibrachoa* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'INCALIMRED'. These characteristics in combination distinguish 'INCALIMRED' as a new and distinct *Calibrachoa* plant:

1. Upright to outwardly spreading and low mounding to eventually trailing plant habit.
2. Vigorous growth habit.
3. Freely branching habit; dense and bushy appearance.
4. Early and freely flowering habit.
5. Large dark red-colored petals with a dark burgundy-colored central band and yellow-colored centers.
6. Good garden performance.

The new *Calibrachoa* plant can be compared to plants of the female parent, 'Duealcher'. Plants of the new *Calibrachoa* differ primarily from plants of 'Duealcher' in plant size as plants of 'Duealcher' are smaller than plants of the new *Calibrachoa*. In addition, leaves of plants of the new *Calibrachoa* are darker green in color than leaves of plants of 'Duealcher'.

The new *Calibrachoa* plant can be compared to plants of the male parent selection. Plants of the new *Calibrachoa* differ primarily from plants of the male parent selection in flower size as plants of the male parent selection have smaller flowers than plants of the new *Calibrachoa*. In addition, leaves of plants of the new *Calibrachoa* are darker green in color than leaves of plants of the male parent selection.

Plants of the new *Calibrachoa* can be compared to plants of the *Calibrachoa* sp. 'Uscali28', disclosed in U.S. Plant Pat. No. 14,847. In side-by-side comparisons, plants of the new *Calibrachoa* differ primarily from plants of 'Uscali28' in the following characteristics:

1. Plants of the new *Calibrachoa* are taller and more upright than plants of 'Uscali28'.
2. Plants of the new *Calibrachoa* flower earlier and more freely than plants of 'Uscali28'.
3. Plants of the new *Calibrachoa* have larger flowers than plants of 'Uscali28'.

Plants of the new *Calibrachoa* can also be compared to plants of the *Calibrachoa* sp. 'USCAL23101', disclosed in U.S. Plant Pat. No. 27,010. In side-by-side comparisons, plants of the new *Calibrachoa* differ primarily from plants of 'USCAL23101' in flower color as plants of 'USCAL23101' have cherry red-colored flowers.

BRIEF DESCRIPTION OF THE PHOTOGRAPHS

The accompanying colored photographs illustrate the overall appearance of the new *Calibrachoa* plant showing the colors as true as it is reasonably possible to obtain in colored reproductions of this type. Colors in the photographs may differ slightly from the color values cited in the detailed botanical description which accurately describe the colors of the new *Calibrachoa* plant.

The photograph at the bottom of the sheet is a side perspective view of a typical flowering plant of 'INCALIMRED' grown in a container.

The photograph at the top of the sheet is a close-up view of a typical flowering plant of 'INCALIMRED'.

DETAILED BOTANICAL DESCRIPTION

The aforementioned photographs and following observations and measurements describe plants grown during the late winter in 10-cm containers in an acrylic-covered greenhouse in Carleton, Mich. and under cultural practices typical of commercial *Calibrachoa* production. During the production of the plants, day and night temperatures ranged from 18° C. to 30° C. and light levels averaged 1,500 foot-candles. Plants were seven weeks from planting rooted cuttings when the photographs and description were taken. In the following description, color references are made to The Royal Horticultural Society Colour Chart, 2007 Edition, except where general terms of ordinary dictionary significance are used.

Botanical classification: *Calibrachoa* sp. 'INCALIMRED'.

Parentage:

*Female, or seed, parent.*—*Calibrachoa* sp. 'Duealcher', disclosed in U.S. Plant Pat. No. 25,522.

*Male, or pollen, parent.*—Proprietary selection of *Calibrachoa* sp. identified as code number Ca12-3023-4, not patented.

Propagation:

*Type.*—By vegetative terminal cuttings.

*Time to initiate roots, summer.*—About 12 days at temperatures about 25° C.

*Time to initiate roots, winter.*—About 16 days at temperatures about 25° C.

*Time to produce a rooted plant, summer.*—About 20 days at temperatures about 25° C.

*Time to produce a rooted plant, winter.*—About 20 days at temperatures about 20° C.

*Root description.*—Medium in thickness, fibrous; typically white in color, actual color of the roots is dependent on substrate composition, water quality, fertilizer type and formulation, substrate temperature and physiological age of roots.

*Rooting habit.*—Moderately freely branching; medium density.

Plant description:

*Plant and growth habit.*—Upright to outwardly spreading and low mounding to eventually trailing plant habit; vigorous growth habit; moderate growth rate; freely branching habit with about four primary lateral branches each with secondary branches developing at every node; dense and bushy appearance.

*Plant height.*—About 8 cm.

*Plant diameter.*—About 22 cm by 23 cm.

Lateral branch description:

*Length.*—About 11 cm.

*Diameter.*—About 1.5 mm.

*Internode length.*—About 1.4 cm.

*Strength.*—Strong.

*Aspect.*—Initially upright then outwardly spreading to eventually trailing.

*Texture and luster.*—Pubescent; matte.

*Color, developing.*—Close to 146C.

*Color, developed.*—Close to 146C.

Leaf description:

*Arrangement.*—Before flowering, alternate; after flowering, opposite; leaves simple.

*Length.*—About 2.7 cm.

*Width.*—About 1.1 cm.

*Shape.*—Elliptical.

*Apex.*—Broadly acute to rounded.

*Base.*—Attenuate.

*Margin.*—Entire.

*Texture and luster, upper and lower surfaces.*—Pubescent, minute; matte.

*Venation pattern.*—Pinnate; arcuate.

*Color.*—Developing leaves, upper surface: Close to 146A. Developing leaves, lower surface: Close to 146B. Fully expanded leaves, upper surface: Close to 147A; venation, close to 147B. Fully expanded leaves, lower surface: Close to 147B; venation, close to 146C.

*Petioles.*—Length: About 5 mm. Diameter: About 2 mm. Texture and luster, upper and lower surfaces: Pubescent, minute; matte. Color, upper surface: Close to 146C. Color, lower surface: Close to 146D.

Flower description:

*Flower type and flowering habit.*—Single salverform flowers arising from leaf axils; freely flowering habit with typically about 180 flowers and flower buds developing per plant; flowers face upright to outwardly.

*Fragrance.*—None detected.

*Natural flowering season.*—Early flowering, plants of the new *Calibrachoa* begin flowering about six to seven weeks after planting; plants flower continuously from the spring though the summer until frost.

*Flower longevity.*—Individual flowers last about one week on the plant; flowers persistent.

*Flower buds.*—Length: About 2.2 cm. Diameter: About 6 mm. Shape: Oblong, elongate. Texture and luster: Pubescent, minute; matte. Color: Close to 199C to 199D.

*Flower diameter.*—About 3 cm.

*Flower length (height).*—About 2.7 cm.

*Flower throat diameter.*—About 4 mm by 7 mm.

*Flower tube length*.—About 1.8 cm.

*Flower tube diameter*.—Proximally, about 3 mm; distally, about 6 mm.

*Corolla*.—Arrangement: Five fused petals opening into a flared trumpet. Petal lobe length (from throat): About 1.2 cm. Petal lobe width: About 1.5 cm. Petal shape: Fan-shaped. Petal apex: Rounded. Petal margin: Entire. Petal texture and luster, upper surface: Smooth, glabrous, satiny; mostly matte. Petal texture and luster, lower surface: Pubescent, minute; matte. Throat texture and luster: Smooth, glabrous; slightly glossy. Tube texture and luster: Pubescent, minute and primarily along the veins; matte. Color: Petal lobe, when opening, upper surface: Close to 53A. Petal lobe, when opening, lower surface: Close to 183D. Petal lobe, fully opened, upper surface: Ground color, more saturated than 53A; band surrounding the throat, close to 187B; venation, close to 53A and 187B; with development, ground color becoming closer to 46A. Petal lobe, fully opened, lower surface: Close to 183D; venation, close to 187B and 187D; with development, color becoming closer to 181C. Throat: Close to 15C; venation, close to 199C. Tube: Close to 160C; venation, close to 183B.

*Calyx*.—Arrangement: One star-shaped calyx tube with five sepals fused towards the base and arranged in a single whorl. Length: About 1.7 cm. Diameter: About 1.4 cm. Sepal length: About 1.2 cm. Sepal width: About 3 mm. Sepal shape: Lanceolate. Sepal apex: Acute. Sepal margin: Entire. Sepal texture and luster, upper and lower surfaces: Pubescent, minute; matte. Sepal color, upper and lower surfaces: Close to 146A.

*Peduncles*.—Length: About 2 cm. Diameter: About 1.5 mm. Angle: About 45° from stem axis. Strength: Strong. Texture and luster: Pubescent, minute; matte. Color: Close to 146C.

*Reproductive organs*.—Stamens: Quantity: Five per flower. Filament length: About 1 cm. Filament color: Close to 145C. Anther size: About 1 mm by 1 mm. Anther shape: Round. Anther color: Close to 8B. Pollen amount: Moderate. Pollen color: Close to 4A. Pistils: Quantity: One per flower. Pistil length: About 1.1 cm. Style length: About 9 mm. Style color: Close to 145B. Stigma diameter: About 1 mm. Stigma shape: Oval. Stigma color: Close to 146D. Ovary color: Close to 145A. Seeds and fruits: Seed and fruit development have not been observed on plants of the new *Calibrachoa*.

Garden performance: Plants of the new *Calibrachoa* have been observed to have good garden performance and tolerate wind, rain and to be suitable for USDA Hardiness Zones 9 to 11.

Pathogen & pest resistance: Plants of the new *Calibrachoa* have not been observed to be resistant to pathogens and pests common to *Calibrachoa* plants.

It is claimed:

1. A new and distinct *Calibrachoa* plant named 'INCALIMRED' as illustrated and described.

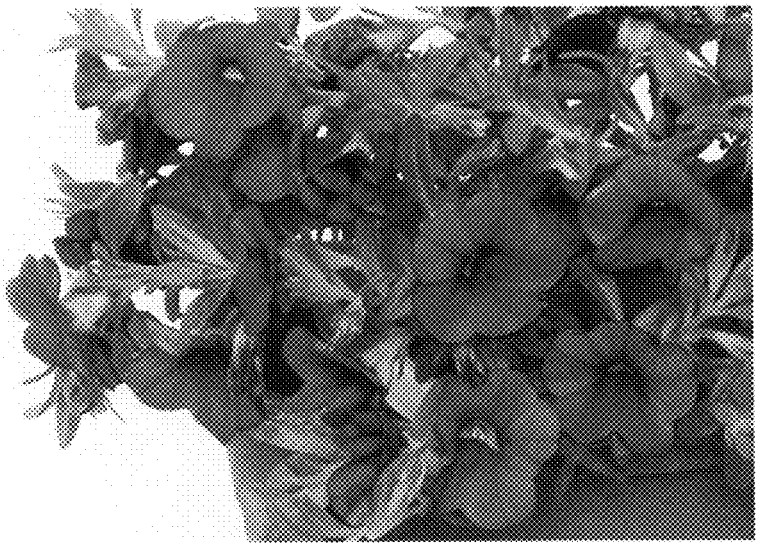
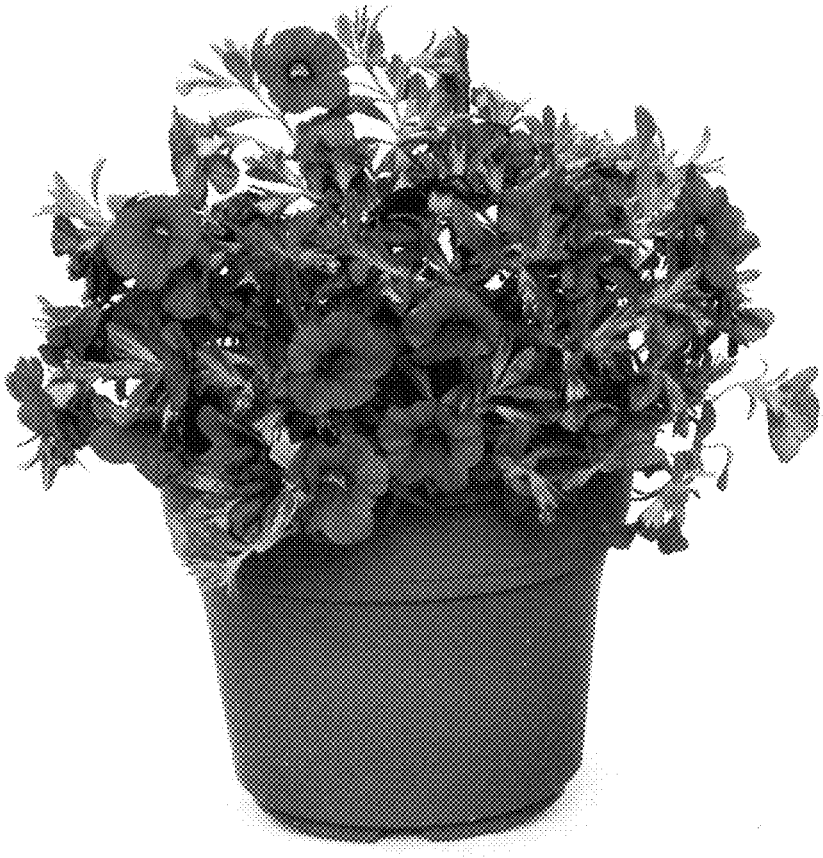

* * * * *